US011045487B2

(12) United States Patent
Ivanova et al.

(10) Patent No.: US 11,045,487 B2
(45) Date of Patent: Jun. 29, 2021

(54) PHARMACEUTICAL PREPARATION TREATING BONE LESIONS CAUSED BY MALIGNANT NEOPLASMS

(71) Applicant: MAXWELL BIOTECH GROUP LTD., Moscow (RU)

(72) Inventors: Ekaterina Alekseevna Ivanova, Moscow (RU); Alexander Karpeisky, Lafayette, CO (US); Shawn P. Zinnen, Denver, CO (US); Lisa Lynn Caralli, Del Mar, CA (US); Rina Diana Fong, San Diego, CA (US)

(73) Assignee: MAXWELL BIOTECH GROUP LTD., Moscow (RU)

( * ) Notice: Subject to any disclaimer, the term of this patent is extended or adjusted under 35 U.S.C. 154(b) by 0 days.

(21) Appl. No.: 16/318,852

(22) PCT Filed: May 5, 2017

(86) PCT No.: PCT/RU2017/050034
§ 371 (c)(1),
(2) Date: Jan. 18, 2019

(87) PCT Pub. No.: WO2018/016999
PCT Pub. Date: Jan. 25, 2018

(65) Prior Publication Data
US 2019/0240245 A1    Aug. 8, 2019

(30) Foreign Application Priority Data

Jul. 20, 2016    (EA) .................................. 201600574

(51) Int. Cl.
| A61K 31/70 | (2006.01) |
| A01N 43/04 | (2006.01) |
| A61K 31/7068 | (2006.01) |
| A61K 47/02 | (2006.01) |
| A61P 35/00 | (2006.01) |
| A61K 31/663 | (2006.01) |
| A61P 19/00 | (2006.01) |
| A61K 9/19 | (2006.01) |
| A61K 9/00 | (2006.01) |
| A61K 9/08 | (2006.01) |
| A61K 47/26 | (2006.01) |

(52) U.S. Cl.
CPC ........ *A61K 31/7068* (2013.01); *A61K 9/0019* (2013.01); *A61K 9/08* (2013.01); *A61K 9/19* (2013.01); *A61K 31/663* (2013.01); *A61K 47/02* (2013.01); *A61K 47/26* (2013.01); *A61P 19/00* (2018.01); *A61P 35/00* (2018.01)

(58) Field of Classification Search
None
See application file for complete search history.

(56) References Cited

U.S. PATENT DOCUMENTS

| 4,810,486 A | 3/1989 | Kelly et al. |
| 5,428,181 A | 6/1995 | Sugioka et al. |
| 6,383,999 B1 | 5/2002 | Coyle et al. |
| 6,896,871 B2* | 5/2005 | Karpeisky ............ A61K 31/675 424/1.77 |
| 9,216,204 B2 | 12/2015 | Karpeisky et al. |
| 2001/0041689 A1 | 11/2001 | Padioukova et al. |
| 2003/0175313 A1 | 9/2003 | Garrec et al. |
| 2010/0160208 A1 | 6/2010 | Schlingensiepen et al. |
| 2013/0184447 A1 | 7/2013 | Piccariello |
| 2014/0051625 A1 | 2/2014 | Karpeisky et al. |
| 2014/0234210 A1 | 8/2014 | Lin et al. |
| 2015/0165027 A1* | 6/2015 | Ikeda ................... A61K 9/0019 514/343 |

FOREIGN PATENT DOCUMENTS

| CA | 2 376 258 | 12/2000 |
| RU | 2 068 262 | 10/1996 |
| RU | 2 116 069 | 7/1998 |
| RU | 2 238 736 | 10/2004 |
| RU | 2 303 997 | 8/2007 |
| RU | 2 433 822 | 11/2011 |
| RU | 2 525 392 | 8/2014 |
| WO | WO 2009/152440 | 12/2009 |
| WO | WO 2012/008845 | 1/2012 |

OTHER PUBLICATIONS

Gega et al. Journal of Clinical Oncology (2006), vol. 24, pp. 102-105.*
International Search Report issued in PCT/RU2016/050076 dated Mar. 6, 2017.
International Preliminary Report on Patentability issued in PCT/RU2016/050076 dated Jun. 6, 2018.
Office Action issued in U.S. Appl. No. 15/780,384 dated Jul. 11, 2019.
AAT, HBSS (Hank's Balanced Salt Solution) recipe and preparation: retrieved from internet on Feb. 25, 2019 https://www.aatbio.com/resources/buffer-preparations-and-recipes/hbss-hanks-balanced-salt-solution.

(Continued)

*Primary Examiner* — Patrick T Lewis
(74) *Attorney, Agent, or Firm* — Nixon & Vanderhye P.C.

(57) ABSTRACT

This invention relates to oncology, and specifically to a novel medicinal drug and a method for treating bone lesions caused by malignant neoplasms. A medicinal drug that represents a lyophilisate for solution for parenteral administration, including the following components: pharmaceutically acceptable salt of the divalent metal and 1-(((((2R, 3S,4S,5R)-5-(4-amino-2-oxopyrimidine-1(2H)-yl)-3,4-dihydroxytetrahydrofuran-2-yl)methoxy))(hydroxy) phosphoryloxy)(hydroxy)phosphoryl)-1-hydroxyethylphosphonic acid or pharmaceutically acceptable salt hereof with a molar ratio of the components ranging from 1:1 to 20:1 is proposed for this purpose. The treatment method includes the drug solution administration according to the invention in the form of intravenous drop infusions in a dose ranging from 0.01 to 5 mg/kg of the active component per 1 kg of the patient's weight in the form of intravenous drop infusions. The treatment with the medicinal drug according to the invention allows to reduce the metabolic activity of bone lesions caused by malignant tumours up to 100%.

19 Claims, 3 Drawing Sheets

(56) References Cited

OTHER PUBLICATIONS

Magnesium Sulfate in 5% Dextrose Injection, Retrieved on Jul. 8, 2019, USP: http://wgcriticalcare.com/wp-content/uploads/2016/09/WGCC_Mag_Sulf_Dex_PI_Rev_Nov_2015.pdf.

Meier, "Nucleoside diphosphate and triphosphate prodrugs—An unsolvable task?" *Antiviral Chemistry and Chemotherapy*, vol. 25, No. 3: 69-82 (2017).

PanReac AppliChem, Hanks' balanced salts (HBSS), Product No. A3140, retrieved on Jul. 8, 2019, <https://www.itwreagents.com/download_file/product_infos/A3140/en/A3140_en.pdf>.

A Trial of MBC-11 in Patients With CIBD, Feb. 3, 2016, https://www.bioportfolio.com/resources/trial/152422/A-Trial-of-MBC-11-in-Patients-With-CIBD.html.

Farrell et al., "Bisphosphonate conjugation for bone specific drug targeting" *Bone Reports*, 9 (2018) 47-60.

Ora et al., "Bisphosphonate Derivatives of Nucleoside Antimetabolites: Hydrolytic Stability and Hydroxyapatite Adsorption of 5'-β,γ-Methylene and 5'-β,γ-(1-Hydroxyethylidene) Triphosphates of 5'-Fluorouridine and ara-Cytidine" *J. Org. Chem.*, 2008, 73, 4123-4130.

Reinholz et al., "A Promising Approach for Treatment of Tumor-Induced Bone Diseases: Utilizing Bisphosphonate Derivatives of Nucleoside Antimetabolites" *Bone*, Jul. 2010; 47(1): 12-22, doi:10.1016/j.bone.2010.03.006.

Schenkein et al., "Accelerated Bone Formation Causing Profound Hypocalcemia in Acute Leukemia" *Annals of International Medicine*, 1986;105: 375-378.

Zinnen et al., "Phase 1 study of the bone-targeting cytotoxic conjugate, etidronate-cytosine arabinoside (MBC-11), in cancer patients with bone metastases" *J Clin. Oncol*, 2017, 35:15_suppl, 2589.

A Trial of MBC-11 in Patients With CIBD, Feb. 3, 2016, 2 pages.

Office Action issued in U.S. Appl. No. 15/780,384 dated Sep. 18, 2020.

Williams, "Magnesium Ion Catalyzed ATP Hydrolysis" *J. Am. Chem. Soc.*, vol. 122, No. 48: 12023-12024 (2000).

* cited by examiner

PHARMACEUTICAL PREPARATION TREATING BONE LESIONS CAUSED BY MALIGNANT NEOPLASMS

This application is the U.S. national phase of International Application No. PCT/RU2017/050034 filed May 5, 2017 which designated the U.S. and claims priority to EA Application No. 201600574 filed Jul. 20, 2016, the entire contents of each of which are hereby incorporated by reference.

FIELD OF THE INVENTION

This invention relates to oncology, and specifically to a novel medicinal drug and a method for treating bone lesions caused by malignant neoplasms.

BACKGROUND OF THE INVENTION

Metastatic bone lesion is one of the most frequent manifestations of malignant neoplasms. They accompany breast cancer, thyroid cancer, prostate cancer, kidney cancer and lung cancer most frequently. Gastrointestinal tract tumours, ovarian cancer, melanomas and lymphomas, although less frequently but they can also metastasize into the bones. Multiple tumour bone lesion of is one of the main manifestations of multiple myeloma. Bone metastases burden the patients' state significantly, causing pain, pathological fractures. The spinal cord compression symptoms and extremity paresis or paralysis symptoms as well as pelvic disorders occur when the spine is damaged. Primary malignant bone tumours are relatively less often, such diseases include, in particular, osteosarcoma, Ewing sarcoma, chondrosarcoma, fibrosarcoma.

Cytarabine is a drug from the group of antimetabolites—pyrimidine nucleoside analogues, which is an effective cytostatic used in the treatment of malignant diseases such as myeloid leukemia, lymphogranulomatosis, erythromyelosis, neuroleukemia, non-Hodgkin's lymphomas. However, its use in the treatment of solid tumours and metastases hereof is limited due to the impossibility of its delivery to the target of the action in the concentration necessary for the tumour destruction.

Bisphosphonates are synthetic analogues of pyrophosphates and are characterized by a phosphorus-carbon-phosphorus bond (in comparison with a phosphorus-oxygen-phosphorus bond in pyrophosphate) present in the molecule backbone structure, which provides for their hydrolytic stability, as well for the suitability for the treatment of degenerative bone diseases. The chemical and biological properties of bisphosphonates vary depending on the various substituents of the carbon atom in the phosphorus-carbon-phosphorus bond.

Bisphosphonates possess a high chemical affinity for hydroxyapatite, as a result, they inhibit the activity of osteoclasts—cells whose function is bone resorption binding on the bone surface. Bisphosphonates can also affect osteoblasts, which play an important role in bone formation. Therefore, bisphosphonates are used in clinical practice to inhibit bone tissue resorption in diseases such as Paget's disease, osteoporosis, metastatic bone tissue lesions, as well as benign and malignant hypercalcemia (see, for example, U.S. Pat. Nos. 5,428,181, 7,645,459). Bisphosphonates are also used to control the adverse effects of antitumor therapy, changing the bone surface and its microenvironment, inhibiting specific enzymatic chains and stimulating apoptosis of osteoclasts and tumour cells. The use of bisphosphonates, in addition to chemotherapy, hormone therapy and radiation therapy, became a modern international standard for treating patients with bone metastases of malignant tumours, as well as treating patients with multiple myeloma. However, bisphosphonates do not have a direct cytostatic effect on tumour cells in pharmacologically acceptable concentrations.

The delivery of a chemotherapeutic agent in the concentration necessary for the tumour destruction into bone tissue is one of the unsolved problems in the treatment of bone lesions caused by malignant neoplasms. Search for a combination of maximum efficacy and acceptable toxicity is a difficult task for researchers in anticancer drug development.

To solve such a task, a conjugate of two molecules: etidronate-bisphosphonate with properties aimed at prevention of bone destruction, and cytarabine—a cytotoxic agent that destroys tumour cells (U.S. Pat. Nos. 8,586,781, 9,216,204; Monica M. Reinholz et. al., A promising approach for treatment of tumor-induced bone diseases: utilizing bisphosphonate derivatives of nucleoside antimetabolite //. Bone., 2010, 47(1),12-22) has been developed and synthesized chemically.

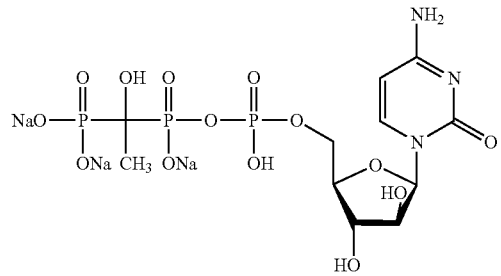

Trisodium salt of 1-((((((2R,3S,4S,5R)-5-(4-amino-2-oxopyrimidine-1(2H)-yl)-3,4-dihydroxytetrahydrofuran-2-yl)methoxy))(hydroxy)phosphoryloxy)(hydroxy)phosphoryl)-1-hydroxyethylphosphonic acid
(MBC-11)
$C_{11}H_{17}N_3Na_3O_{14}P_3$ (Mr=577.15 g/mol)

The mode of action of the drug substance represented by the etidronate-cytarabine conjugate is based on the ability of the bisphosphonate moiety to direct the conjugate to the sites of bone destruction. The conjugate stability in the blood flow after intravenous administration is such that it provides the time necessary to release the antitumor agent mainly into the bones. When the drug substance finds its way to the site of bone destruction, it is hydrolysed with the formation of cytarabine and etidronate, each of which affects the invaded tissues: cytarabine inhibits the tumor growth, and the bisphosphonate suppresses the bone resorption caused by the effect of cancer cells concentrated on the bone surface.

However, the clinical use of the etidronate-cytarabine conjugate is impossible as yet, due to the fact that the conjugate is unstable both in acid medium (which, combined with low bioavailability, complicates its oral administration), and in aqueous solutions (which complicates its parenteral administration).

Despite numerous studies in this area, the problem of targeted delivery of a chemotherapeutic agent into bone tissue in the concentration necessary for the tumour destruction and the effective treatment of bone lesions caused by malignant neoplasms is still unsolved.

SUMMARY OF THE INVENTION

The object of this invention is the creation the medicinal drug and the development of an effective method for treating patients with bone lesions caused by malignant tumours.

The said task is solved by creating a novel medicinal drug for treating bone lesions caused by malignant tumours, which is a lyophilisate for solution for parenteral administration, including the following components:
pharmaceutically acceptable salt of the divalent metal and etidronate conjugate with cytarabine (1-((((((2R,3S,4S,5R)-5-(4-amino-2-oxopyrimidine-1(2H)-yl)-3,4-dihydroxytetrahydrofuran-2-yl)methoxy))(hydroxy)phosphoryloxy)(hydroxy)phosphoryl)-1-hydroxyethyl phosphonic acid) or a pharmaceutically acceptable salt thereof,
with a molar ratio of the components ranging from 1:1 to 20:1.

In certain embodiments, the divalent metal salt is magnesium chloride or calcium chloride.

In a part of embodiments, the pharmaceutically acceptable salt of etidronate conjugate with cytarabine is a trisodium salt.

In certain embodiments, the molar ratio of the components is ranging from 1:1 to 12:1.

In some particular embodiments, the molar ratio of the components is ranging from 1:1 to 2:1.

In some the most preferred embodiments, the molar ratio of the components is 2:1.

The said task is also solved by using the etidronate conjugate with cytarabine for treating bone lesions caused by malignant neoplasms.

The said task is also solved by developing a method for treating bone lesions caused by malignant neoplasms, including parenteral administration of a solution of a medicinal drug according to the invention in a pharmaceutically acceptable solvent.

In some embodiments, the pharmaceutically acceptable solvent is a 5% aqueous dextrose (glucose) solution and/or sterile water for injections.

In preferred embodiments, the administration in the form of an intravenous drop infusion is used as parenteral administration.

In certain embodiments, the concentration of etidronate conjugate with cytarabine on free acid basis in the solution for administration is ranging from 0.01 mg/ml to 5 mg/ml.

In some particular embodiments, the concentration of etidronate conjugate with cytarabine on free acid basis in the solution for administration is ranging from 0.04 mg/ml to 2 mg/ml.

In particular embodiments, the medicinal drug is administered in a dose ranging from 0.5 to 5 mg of etidronate conjugate with cytarabine on free acid basis per 1 kg of patient's weight in the form of intravenous drop infusion.

In some particular embodiments, a solution of the medicinal drug in a volume of 500 ml is administered to a patient.

In some embodiments, the infusions are administered in cycles: daily administration during 5 days followed by a break of at least 23 days.

In some particular embodiments, the infusions are administered in cycles: daily administration during 5 days followed by a break during 23-40 days.

In some other embodiments, the infusions are administered in cycles: 3 administrations every other day followed by a break of at least 23 days.

In some other embodiments, the infusions are administered in cycles: at least one administration per week for 12 months In some other embodiments, the infusions are administered in cycles: at least one administration per month for 12 months.

In some embodiments, the number of cycles is ranging from 1 to 12 per a treatment course.

In some particular embodiments, the number of cycles is ranging from 1 to 6 per a treatment course.

The said task is also solved by using the etidronate conjugate with cytarabine to produce medicinal drug (preparation) for treating bone lesions caused by malignant neoplasms.

This object is also solved by obtaining a medicinal drug (preparation) for treating bone lesions caused by malignant tumours, which includes the following steps:
preparing an aqueous solution comprising etidronate conjugate with cytarabine or pharmaceutically acceptable salt hereof and a stabilizer, which is a divalent metal salt, wherein the molar ratio of the stabilizer and the conjugate choosing from 1:1 to 20:1;
conducting a sterile filtration of the obtained solution;
pouring the obtained solution into containers for lyophilization;
conducting lyophilization.

In particular embodiments, the bone lesion caused by malignant neoplasms is a primary bone cancer, for example, osteosarcoma, Ewing sarcoma, chondrosarcoma, fibrosarcoma, malignant fibrous histiocytoma, giant-cell tumour of the bone or chordoma.

In other particular embodiments, the bone lesion caused by malignant neoplasms is multiple myeloma, metastatic bone tissue lesions caused by breast cancer, prostate cancer or thyroid cancer, lung cancer, kidney cancer, gastrointestinal cancer, ovarian cancer, melanoma, lymphoma, or malignant neoplasms in other tissues and organs.

During the implementation of the invention, the following technical results are achieved:
a dosage form of etidronate conjugate with cytarabine or pharmaceutically acceptable salt hereof has been developed, ensuring its stability during long-term storage;
solutions for parenteral administration of etidronate conjugate with cytarabine or pharmaceutically acceptable salt hereof have been developed; they possess hydrolytic and physical stability when used;
a novel effective and safe medicinal drug has been developed to treat patients with bone lesions caused by malignant neoplasms;
a novel effective method has been developed to treat bone lesions caused by malignant neoplasms.

DEFINITIONS (TERMS)

Figure 1:
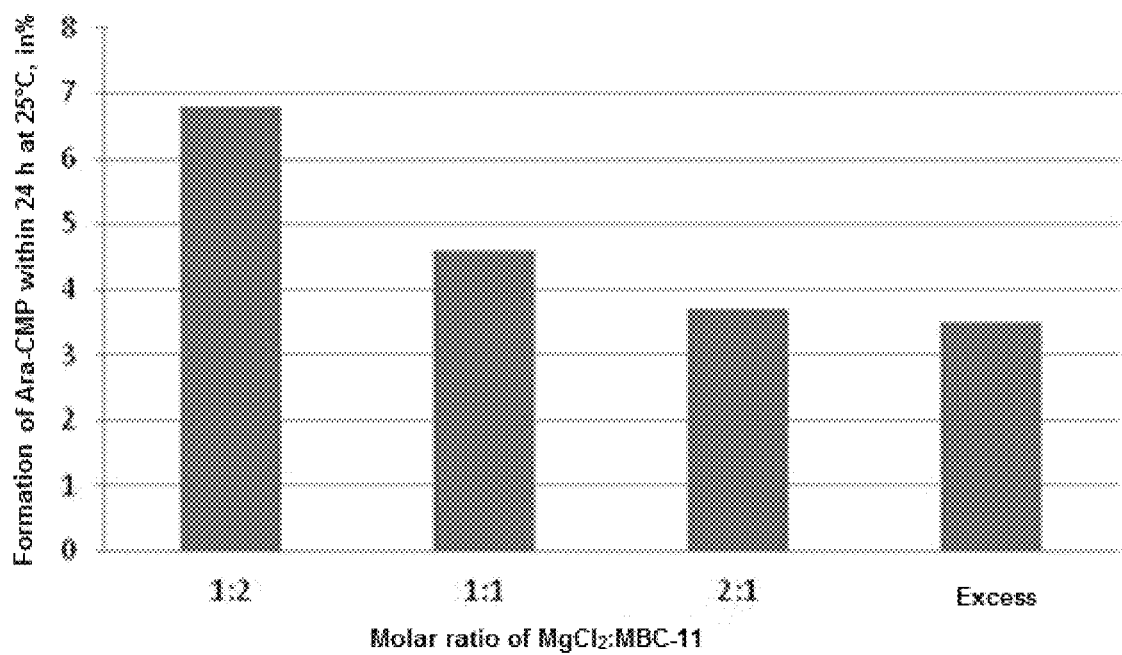
FIG. 1. The effect of magnesium chloride on the formation of arabinosylcytosine monophosphate (Ara-CMP) in an aqueous solution of the trisodium salt of the etidronate-cytarabine conjugate (MBC-11). The term "Excess" refers to the ratio of MgCl2:MBC-11 of 12:1
Figure 2:
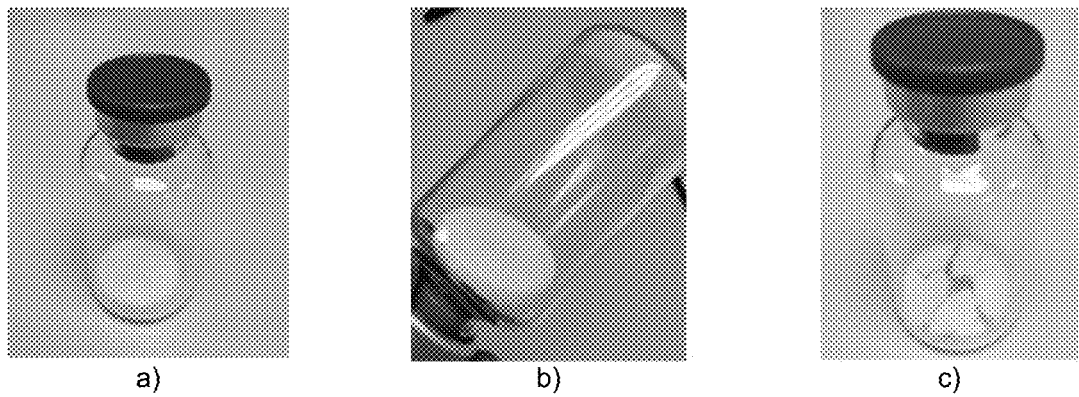
FIG. 2. 20 mL vials with lyophilized dosage form; MBC-11 concentration is 50 mg/mL, the vial is filled to 2 mL. The photos presented demonstrate the type of sintered material: a) compression; b) free movement when the vial is turned upside-down; c) about 40% of all vials in this experiment contain cracked material.
Figure 3:
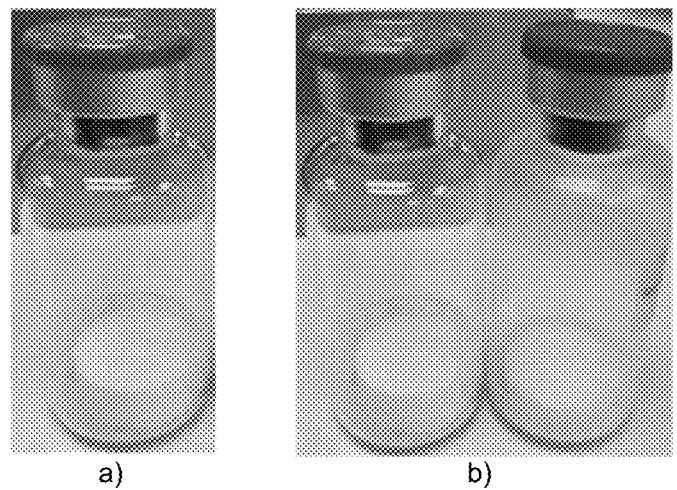
FIG. 3. 20 mL vials with lyophilized dosage form: a) MBC-11 concentration is 20 mg/mL, the vial is filled to 5 mL; b) MBC-11 concentration is 20 mg/mL, the vial is filled to 5 mL (left), in comparison with the MBC-11 concentration of 50 mg/mL, the vial is filled to 2 mL (right).
Figure 4:
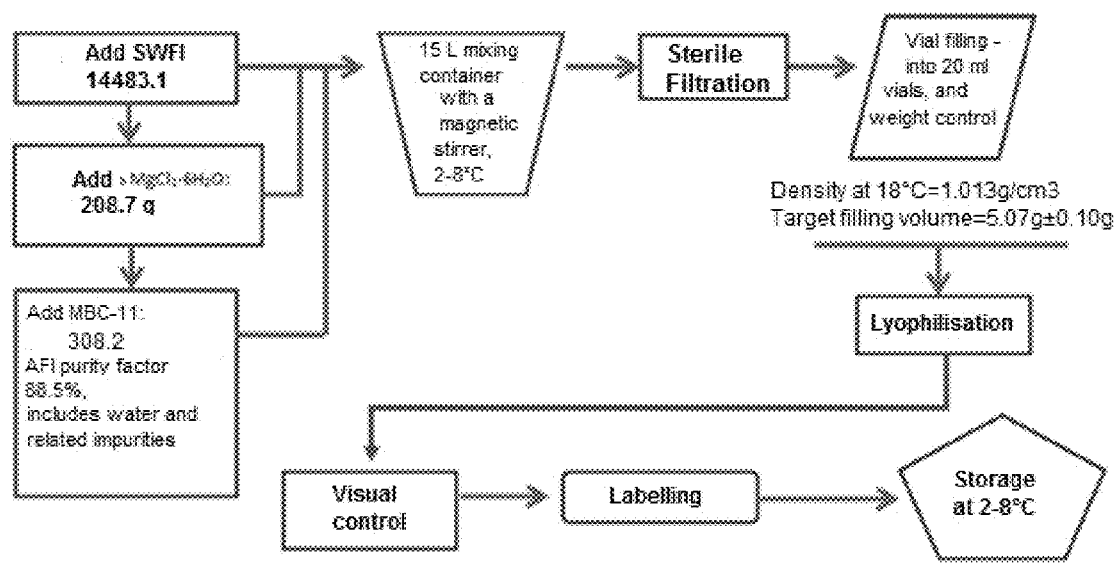
FIG. 4. The diagram of producing a batch of the finished medicinal product of the present invention in the amount of 15 liters (~3000 vials with the filling volume of 5.0±0.1 mL).

The term "MBC-11" used herein refers to trisodium salt of etidronate conjugate with cytarabine.

"Etidronate conjugate with cytarabine" (i.e., free acid) is a molecule obtained by conjugating two molecules—etidronate(1-hydroxyethane-1,1-diyl) bis(phosphonic acid) and cytarabine(4-amino-1-beta-D-arabinofuranosyl-2 (1H)-pyrimidinone; [1-[[[(2R,3S,4S,5R)-5-(4-amino-2-oxopyridin-1-yl)-3,4-dihydroxyoxolan-2-yl]methoxy-hydroxyphosphoryl]oxy-hydroxyphosphoryl]-1-hydroxyethyl]phosphonic acid) and is called as 1-(((((2R,3S,4S,5R)-5-(4-amino-2α-oxopyrimidine-1(2H)-yl)-3,4-dihydroxytetrahydrofuran-2-yl)methoxy)(hydroxy) phosphoryloxy)(hydroxy)phosphoryl)-1-hydroxyethylphosphonium acid in IUPAC nomenclature.

Trisodium salt of etidronate conjugate with cytarabine (MBC-11) is a compound which has the following chemical formula:

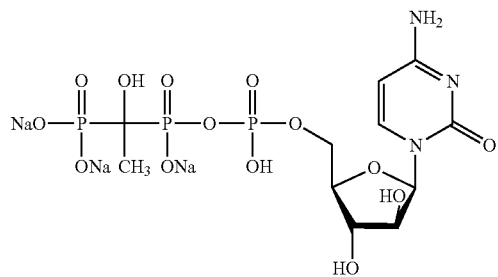

$C_{11}H_{17}N_3Na_3O_{14}P_3$
(Mr=577.15 g/mol)
and the name: trisodium salt of 1-((((((2R,3S,4S,5R)-5-(4-amino-2-oxopyrimidine-1(2H)-yl)-3,4-dihydroxytetrahydrofuran-2-yl)methoxy))(hydroxy)phosphoryloxy)(hydroxy)phosphoryl)-1-hydroxyethylphosphonic acid in IUPAC nomenclature.

As used herein, the term "pharmaceutically acceptable salt" refers to those salts, which, within the scope of the medical assessment performed, are suitable to contact with human and animal tissues without excessive toxicity, irritation, allergic reaction, etc., and meet a reasonable risks and benefits ratio. Non-limiting examples of pharmaceutically acceptable salts of the invention include trisodium, disodium, monosodium, trilithium, dilithium, monolithium salts, etc.

As used herein, the term "divalent metal salts" refers to inorganic and organic calcium and magnesium salts. Examples of acceptable and non-toxic acid salts include salts formed with inorganic acids, such as hydrochloric, hydrobromic or perchloric acid, or with organic acids such as acetic, citric or maleic acids.

As used herein, the term "pharmaceutically acceptable solvent" refers to solvents that are not toxic or harmful to the patient when used in the compositions of this invention, including parenteral administration using methods described herein. It is understood that the solvent should be able to dissolve the appropriate amount of the dosage form of the invention, preferably at moderate stirring at room temperature. Examples of pharmaceutically acceptable solvents within the scope of the present invention may include sterile water for injection, dextrose (glucose) 5% in water (D5W), normal saline solution, in particular isotonic saline solution, and others.

"Parenteral administration" herein refers to intravenous, intra-arterial, intramuscular, intraosseous, intra-articular, subcutaneous or intrathecal administration. The administration can performed by injections of a small volume (up to 100 ml) or by infusion, in particular, by intravenous drop infusion (intravenous drop injection).

The term "therapeutically effective amount (therapeutic dose)" means the amount of a drug substance (or medicinal product) administered or rendered to a patient, and the administration of which is most likely to cause the patient to develop the expected therapeutic effect. The exact amount required may vary from subject to subject depending on the patient's age, body weight and performance status, disease severity, mode of drug administration, combination treatment with other drugs, etc. In particular, doses of 0.001 to 50 mg/kg are therapeutically effective for the etidronate-cytarabine conjugate, or a pharmaceutically acceptable salt thereof, more preferably—from 0.001 to 25 mg/kg. Herewith, the term "patient" means a human or an animal, whose disease needs to be treated or prevented by means of the conjugate. The etidronate-cytarabine conjugate, or a pharmaceutically acceptable salt thereof, is administered to a patient needed to treat at a dose sufficient to achieve a therapeutic effect.

In the course of treatment the dose can be administered one or several times a day, a week (or any other time interval). Additionally, the medicinal drug can be administered to a patient each day for a certain period (for example, 2-10 days), followed by a period without taking any medicinal drug (for example, 1-30 days). The treatment regimen, as well as the duration of treatment, can also vary from patient to patient and range from the minimum course of treatment to conducting treatment by courses throughout the patient's life.

Different embodiments relate to a novel medicinal drug (preparation), which is a stabilized dosage form of etidronate conjugate with cytarabine according to the invention and its use to treat bone lesion caused by a malignant neoplasm, including primary bone cancer.

Embodiments are also provided by methods for treating bone lesions caused by malignant neoplasms. The method includes parenteral administration to a patient of a therapeutically effective amount of the medicinal drug according to the invention in the form of a solution in a pharmaceutically acceptable solvent. In most preferred embodiments, the drug solution according to the invention is administered in the form of intravenous drop infusions. In different embodiments, bone lesions caused by malignant neoplasms may include multiple myeloma, osteosarcoma, metastatic lesions of bone tissue caused by breast cancer, prostate cancer, thyroid cancer or cancer of other tissues and organs. In other embodiments, bone lesions caused by malignant neoplasms may be primary bone cancer, including, but not limited to, osteosarcoma, Ewing sarcoma, chondrosarcoma fibrosarcoma, malignant fibrous histiocytoma, giant-cell tumour of the bone or chordoma. In different embodiments, the medicinal drug according to the invention can be administered to patients in combination with other drugs in various therapy regimens, as well as in combination with other therapy methods, such as, for example, radiation therapy or surgical treatment.

The present invention also relates to a kit comprising a lyophilized dosage form of the etidronate-cytarabine conjugate in a container, an aqueous solution or a dextrose 5% solution, inline filters. The dosage form is suitable for parenteral administration of effective doses of the conjugate, as well as for infusion administration, i.e. for aseptic connection with intravenous valves, tubes, parts, lines, etc., or for transportation of the drug between infusion devices.

The kit may also include one or more dosage forms packed together with instruction materials relating to the administration of the dosage form or with instruction materials including labeling instrumentation, for example labels, tags, CDs, DVDs, recorded cassettes, etc. describing the use of the drug form in a manner approved by the government regulatory body.

Thus, the dosage form in the present invention provides one or more unit drug doses, adapted to the practice of the method of administration, which comprise an etidronate-cytarabine conjugate, or a pharmaceutically acceptable salt thereof, at a suitable concentration in a biocompatible carrier packaged to maintain sterility and to protect the active ingredient from degradation.

The possibility of the objective manifestation of the technical result when the invention is used is confirmed by valid data given in the examples containing experimental data obtained during research according to the methods adopted in this area. The nature of the invention is explained by figures.

The following examples are provided for the purpose of illustrating the method according to the this invention and should not be considered as limiting the scope of the invention in any way.

DETAILED SPECIFICATION

For the invention of the pharmaceutical compositions suitable for parenteral administration, the aqueous solution of the finished dosage form of the medicinal product must have a stability that provides a time sufficient for its clinical preparation, short-term storage and use. In addition, the finished form itself must be sufficiently stable for long-term storage.

It has been established the stability of pharmaceutical compositions in long-term storage can be achieved by means of lyophilization. The studies performed have shown that the administration of divalent metal salts slightly increases the hydrolytic stability of aqueous solutions of the etidronate-cytarabine conjugate, or pharmaceutically acceptable salts thereof. However, none of the above said approaches provides for a stable dosage form of the etidronate-cytarabine conjugate, or a pharmaceutically acceptable salt thereof, for parenteral administration. The combined use of these two approaches is, then, complicated by the fact that divalent cations tend to reduce the glass transition temperature, which exacerbates the lyophilization process. In addition, divalent cations cause physical instability (contribute to sedimentation) of reconstituted lyophilizate solutions.

As a result of the studies performed, it was unexpectedly found that if divalent metal salts are used in solutions of the etidronate-cytarabine conjugate, or a pharmaceutically acceptable salt thereof, the effect of divalent cations on the production of a stable dosage form depends on the ratio of divalent metal salts and conjugate in the solution for lyophilization, that the favorable ratio of stabilizer to conjugate is at least 1:1, more optimal is the ratio from 1:1 to 20:1, even more optimal—from 1:1 to 12:1, and even more optimal—from 1:1 to 2:1. With this ratio of components, not only the hydrolytic stability of the conjugate is ensured, but also the effective completion of all stages of its lyophilization process. The resulting lyophilizates remain stable for a long time (up to several years) and have optimum solubility, and the solutions resulted from them are physically and hydrolytically stable for several hours, which makes it possible to use them for parenteral administration during clinical use of same.

The possibility of an objective demonstration of the technical result, when the invention is used, is confirmed by reliable data given in the examples containing experimental data obtained in the course of research on the methods adopted in this field. The nature of the invention is illustrated by the figures.

It should be understood, that these and all of the examples provided in the application materials are not intended to be limiting and are given only to illustrate the present invention.

Investigation of the Influence of Divalent Magnesium and Calcium Cations on the Hydrolytic Stability of the Etidronate-Cytarabine Conjugate The ability of divalent metal ($MgCl_2$ and $CaCl_2$) salts to inhibit the hydrolysis of the etidronate-cytarabine conjugate was studied.

The present invention displays specific conjugate concentrations and ratios of divalent metal salts and conjugate, which have all at once allowed to stabilize the drug in an aqueous solution and achieve optimum lyophilization conditions.

Studies were performed, where magnesium chloride was investigated as a stabilizer against hydrolytic decomposition. $MgCl_2$ was added to solutions of MBC-11 conjugate in water, tartrate buffer (50 mmol/L, pH 5) and succinate buffer (50 mmol/L, pH 5). The following molar ratios of $MgCl_2$ to MBC-11 were used: (1:2), (1:1), (2:1) and higher (~12:1). To assess the degree of hydrolysis, the formation of arabinosylcytosine monophosphate (Ara-CMP) (in %) was recorded 24 hours later at 25° C.

The addition of $MgCl_2$ to the conjugate solutions resulted in a marked improvement in the stability of the conjugate. Several samples, mainly in water, showed an increase in Ara-CMP content of only 0.2% 8 hours later at 25° C., as compared to previous observations with an increase of ~2% (Table 1). In general, samples prepared in water were more stable than those prepared using buffer solutions. The exceptions were the samples with a large excess of $MgCl_2$, for which the stability of the conjugate in buffer solutions and water was relatively comparable.

TABLE 1

Effect of $MgCl_2$ on the formation of Ara-CMP at 25° C.

| Buffer Solution | $MgCl_2$ concentration (mmol/L) | Molar ratio of $MgCl_2$:MBC-11 | Content of Ara-CMP (%) | | | |
|---|---|---|---|---|---|---|
| | | | t* = 0 | t = 4 | t = 8 | t = 24 |
| Tartrate | — | — | 3.8 | 5.3 | 6.6 | 11.7 |
| | 0.87 | 1:2 | 2.5 | 3.5 | 4.5 | 8.4 |
| | 1.73 | 1:1 | 2.6 | 3.3 | 4.1 | 7.3 |
| | 3.5 | 2:1 | 2.5 | 3.0 | 3.5 | 5.5 |
| | 20 | ~12:1 | 2.6 | 2.7 | 3.0 | 3.8 |
| Succinate | — | — | 3.5 | 5.0 | 6.4 | 11.5 |
| | 0.87 | 1:2 | 2.6 | 3.5 | 4.4 | 7.9 |
| | 1.73 | 1:1 | 2.5 | 3.1 | 3.7 | 5.6 |
| | 3.5 | 2:1 | 2.6 | 3.1 | 3.7 | 5.8 |
| | 20 | ~12:1 | 2.5 | 2.7 | 2.9 | 3.6 |

TABLE 1-continued

Effect of MgCl$_2$ on the formation of Ara-CMP at 25° C.

| Buffer Solution | MgCl$_2$ concentration (mmol/L) | Molar ratio of MgCl$_2$:MBC-11 | Content of Ara-CMP (%) | | | |
|---|---|---|---|---|---|---|
| | | | t* = 0 | t = 4 | t = 8 | t = 24 |
| Water | 0.87 | 1:2 | 2.6 | 3.3 | 4.0 | 6.8 |
| | 1.73 | 1:1 | 2.5 | 2.8 | 3.2 | 4.6 |
| | 3.5 | 2:1 | 2.7 | 2.7 | 2.9 | 3.7 |
| | 20 | ~12:1 | 2.6 | 2.7 | 2.9 | 3.5 |

*t—time (hour)

According to the results of the experiment, a high hydrolytic stability of the conjugate is provided at a molar ratio of MgCl$_2$ to conjugate of 1:1. As shown in table, the use of water as a solvent and the molar ratio of MgCl$_2$ to MBC-11 of 2:1 provides for the highest stability of the conjugate in aqueous solutions. At higher MgCl$_2$ concentrations, there was a slight decrease in the effect, but the stability remained at a high level (FIG. 1).

The use of calcium chloride as a stabilizer against hydrolytic decomposition in both buffer solutions and water was also investigated; the hydrolysis rate constant was compared with the constant for MgCl$_2$. In water, at a molar ratio of MgCl$_2$ or CaCl$_2$) to MBC-11 of 2:1, the hydrolysis rate constants turned out to be similar (K=0.0005) and significantly exceeded the values for the aqueous solution of the trisodium salt of the etidronate-cytarabine conjugate not containing the above said salts (K=0, 0044). If molar ratios were less than 2:1, the hydrolysis rate was lower for solutions containing MgCl$_2$.

The addition of divalent metal salts to the aqueous solution of MBC-11 in a molar ratio of 2:1 leads to a slowdown in the hydrolysis reaction by 90%. Thus, the preferred ratio of the divalent metal salt to the etidronate-cytarabine conjugate shall be 2:1, but the positive effect of salts on the hydrolytic stability is manifested even at a ratio of 1:1 and is preserved at a ratio of more than 2:1 (at a ratio of 12:1 and higher).

Thermal Behavior of Solutions for Lyophilization

The thermal properties of the solutions provided for lyophilization were investigated.

Differential Scanning calorimetry (DSC) was used to identify the lowest possible transient temperature in the solution throughout the entire lyophilization process, including freezing and dehydration. For the solutions of most pharmaceutical products, this parameter is represented by the glass transition temperature or "$T_{g'}$". All components and their amounts in the solution contribute to the final value of $T_{g'}$. This temperature is usually several degrees below the temperature at which the sintered material can crumble during the lyophilization process (collapse temperature, $T_c$). Without determining the collapse temperature by such methods as cryomicroscopy, the glass transition temperature can be used to select the primary drying temperature. Until the primary drying is completed, the initial drying temperature should be set in such a manner that there are no vials for which the glass transition temperature has been exceeded (or $T_c$, if known). Otherwise, the structure of the sintered material may get broken. On the one hand, the lyophilization temperature should be close to $T_{g'}$, so that the process proceeds efficiently, and on the other hand, it cannot exceed $T_{g'}$ due to process requirements and qualitative product parameters. Thus, the values of collapse and glass transition temperature are important parameters for calculating safe upper temperature limits, which can be used for lyophilization. Based on the proposed filling of the vials with the drug (100 mg of active ingredient per vial), potential solutions for filling were prepared. The excipients included sterile water for injection (SWFI), 50 mM succinate and tartrate buffers at pH 5, MgCl$_2$, sulfobutylether β-cyclodextrin (SBEβCD), mannitol and dextran 40. In addition, for solutions containing mannitol, a study of the effect of the annealing stage (the lyophilization process stage when the samples are kept at a certain temperature below the freezing point for a certain period of time) on the improvement the crystallinity of the finished product was performed. The DSC results are shown in Table 2.

TABLE 2

Thermal behaviour of solutions for lyophilization

| Solvent | MBC-11 (mg/mL) | Excipient | pH | Thermal effect (event) |
|---|---|---|---|---|
| SWFI | 50 | — | 5.2 | −21° C. ($T_{g'}$) |
| | 100 | — | 5.4 | −21° C. ($T_{g'}$) |
| | 100 | MgCl$_2$, 173 mmol/L | — | −22° C. (endothermicity) |
| | 100 | MgCl$_2$, 350 mmol/L | — | −26° C. (endothermicity) |
| | 50 | 20% SBEβCD | — | −26° C. ($T_{g'}$) |
| | 50 | MgCl$_2$, 173 mmol/L | 4.23 | −26° C. (endothermicity) |
| | 50 | MgCl$_2$, 86.5 mmol/L | 4.52 | −34° C. ($T_{g'}$) −21° C. (endothermicity) |
| | 25 | MgCl$_2$, 86.5 mmol/L | 4.35 | −26° C. (endothermicity) |
| | 25 | MgCl$_2$, 43.25 mmol/L | 4.59 | −22° C. ($T_{g'}$) −21° C. (endotherm) |
| | 50 | MgCl$_2$, 173 mmol/L Mannitol, 25 mg/mL | — | $T_{g'}$/endothermicity before alloy expansion |
| | 50 | MgCl$_2$, 86.5 mmol/L Mannitol, 25 mg/mL | — | $T_{g'}$/endothermicity before alloy expansion |
| | 25 | MgCl$_2$, 86.5 mmol/L Mannitol, 25 mg/mL | — | $T_{g'}$/endothermicity before alloy expansion |
| | 25 | MgCl$_2$, 43.25 mmol/L Mannitol, 25 mg/mL | — | Possible crystallization at −27° C. |
| | 25 | MgCl$_2$, 43.25 mmol/L Mannitol, 25 mg/mL Annealing at −20° C. | — | None crystallization after temperature processing, specific endothermicity at −22° C. |

TABLE 2-continued

Thermal behaviour of solutions for lyophilization

| Solvent | MBC-11 (mg/mL) | Excipient | pH | Thermal effect (event) |
|---|---|---|---|---|
| | 25 | $MgCl_2$, 43.25 mmol/L Mannitol, 25 mg/mL Annealing at −24° C. | — | None crystallization after annealing was observed, weak endothermicity at −22° C |
| | 100 | $MgCl_2$, 173 mmol/L Dextran-40 5% | — | −29° C. ($T_{g'}$) |
| | 50 | $MgCl_2$, 173 mmol/L Dextran-40 5% | — | −36° C. ($T_{g'}$) |
| | 50 | $MgCl_2$, 86.5 mmol/L Dextran-40 5% | — | −24° C. ($T_{g'}$) |
| | 25 | $MgCl_2$, 86.5 mmol/L Dextran-40 5% | — | −27° C. ($T_{g'}$) |
| | 25 | $MgCl_2$, 43.25 mmol/L Dextran-40 5% | — | −21° C. ($T_{g'}$) |
| Tartrate buffer | 25 | $MgCl_2$, 86.5 mmol/L | 4.48 | −40° C. ($T_{g'}$) −30° C. (crystallization) −22° C. (endothermicity) |
| | 25 | $MgCl_2$, 86.5 mmol/L Mannitol, 25 mg/mL | — | −40° C. ($T_{g'}$) |
| | 25 | $MgCl_2$, 86.5 mmol/L Dextran-40 5% | — | −26° C. ($T_{g'}$) |
| Succinate buffer | 25 | $MgCl_2$, 86.5 mmol/L | 4.52 | −34° C. (crystallization) −26° C. (endothermicity) |
| | 25 | $MgCl_2$, 86.5 mmol/L Mannitol, 25 mg/mL | — | $T_{g'}$/endothermicity before alloy expansion |
| | 25 | $MgCl_2$, 86.5 mmol/L Dextran-40 5% | — | −30° C. ($T_{g'}$) |

The development of endothermicity, later defined as enthalpy relaxation, was typical of most samples containing $MgCl_2$.

Investigation of Chemical Stability of Solutions for Lyophilization

Several solutions for lyophilization were studied in a short-term study of chemical stability at 25° C., given that buffer solutions were not used. The study results are shown in Table 3.

As mentioned earlier, the most stable solutions contain $MgCl_2$ in a molar ratio to the drug substance of 2:1. Samples with a 1:1 ratio are less stable, but still exhibit low values of the hydrolysis constant. It has been found that the presence of mannitol or dextran, contrary to expectations, does not lead to an improvement in chemical stability. In solutions with a concentration of 100 mg/mL, signs of sedimentation were found on the following day, which could affect the purity values listed in the table. The samples given in bold showed sufficient stability to be prospective solutions to be filled into vials for lyophilization. Within 24 hours at 25° C.,

TABLE 3

Chemical stability of solutions for lyophilization

| Ser. No. | MBC-11 (mg/mL) | Excipient | Purity of the main peak according to HPLC in % | | | | Hydrolysis constant (K) |
|---|---|---|---|---|---|---|---|
| | | | *t = 0 | t = 3 | t = 6 | t = 24 | |
| 1 | 100 | — | 91.30 | 90.79 | 89.70 | 84.62 | 0.0032 |
| 2 | 100 | $MgCl_2$, 173 mmol/L (1 × salt) | 91.33 | 91.16 | 90.76 | 86.87 | 0.0022 |
| 3 | 100 | $MgCl_2$, 173 mmol/L + Dextran 5% | 91.37 | 91.27 | 90.73 | 87.84 | 0.0017 |
| 4 | 50 | — | 91.38 | 90.38 | 89.53 | 84.11 | 0.0034 |
| 5 | 50 | $MgCl_2$, 173 mmol/L (2 × salt) | 91.42 | | 90.97 | 90.24 | 0.0005 |
| 6 | 50 | $MgCl_2$, 173 mmol/L (2 × salt) + mannitol, 25 mg/mL | 91.39 | 91.23 | 91.09 | 90.46 | 0.0004 |
| 7 | 50 | 20% SBEβCD | 91.27 | 90.65 | 89.75 | 85.40 | 0.0028 |
| 8 | 50 | $MgCl_2$, 86.5 mmol/L(1 × salt) + Dextran 5% | 91.16 | 90.86 | 90.81 | 89.67 | 0.0007 |
| 9 | 25 | $MgCl_2$, 86.5 mmol/L (2 × salt) + Dextran 5% | 91.11 | 90.93 | 90.87 | 90.16 | 0.0004 |
| 10 | 25 | $MgCl_2$, 43.3 mmol/L(1 × salt) + Dextran 5% | 91.28 | 90.94 | 90.67 | 89.80 | 0.0006 |
| 11 | 25 | Mannitol, 25 mg/mL | 91.24 | 90.16 | 89.35 | 83.71 | 0.0036 |

*t—time (hour)

the content of the etidronate-cytarabine conjugate in these samples decreased by 1-1.5% only.

Alternative Lyophilized Dosage Forms

Several solutions to be filled into the vials have been selected as options for the preparation of the lyophilized dosage form. The dosage forms selected are shown below (Table 4).

TABLE 4

Dosage forms selected

| | MBC-11 (mg/mL) | Excipient, (in SWFI, pH 5) | Hydrolysis rate constant (K) | Thermal characteristic (° C.) | |
|---|---|---|---|---|---|
| A | 50 | $MgCl_2$ (2 × salt) 173 mmol/L | 0.0005 | −26 | Endotherm |
| B | 50 | $MgCl_2$ (2 × salt) mmol/L + mannitol 25 mg/mL | 0.0004 | — | — |
| C | 50 | 20% SBEβCD | 0.0028 | −26 | $T_{gt}$ |
| D | 50 | $MgCl_2$ (1 × salt) 86.5 mmol/L + Dextran 5% | 0.0007 | −24 | $T_{gt}$ |
| E | 25 | $MgCl_2$ (2 × salt) 86.5 mmol/L + Dextran 5% | 0.0004 | −27 | $T_{gt}$ |
| F | 25 | $MgCl_2$ (1 × salt) 43.3 mmol/L + Dextran 5% | 0.0006 | −21 | $T_{gt}$ |

These solutions were lyophilized using a conventional cycle with a primary temperature of the drying shelf set at −26° C. and a secondary drying temperature of 32° C. The annealing stage was not used (Table 5).

TABLE 5

Characteristics of the sintered material

| Form | MBC-11 (mg/mL) | Excipient, in SWFI with pH 5 | Appearance* | Dissolution | Purity before lyophilization (%) | Purity after lyophilization (%) |
|---|---|---|---|---|---|---|
| A | 50 | $MgCl_2$ (2 × salt) 173 mmol/L | 4 | 10 sec | 95.8 | 95.5 |
| B | 50 | $MgCl_2$ (2 × salt) mmol/L + mannitol 25 mg/mL | 5 | 10 sec | 95.9 | 95.7 |
| C | 50 | 20% SBEβCD | 2 | 10 sec | 95.5 | 95.5 |
| D | 50 | $MgCl_2$ (1 × salt) 86.5 mmol/L + Dextran 5% | 3 | 1 min | 95.7 | 95.7 |
| E | 25 | $MgCl_2$ (2 × salt) 86.5 mmol/L + Dextran 5% | 4 | 1 min | 95.8 | 95.8 |
| F | 25 | $MgCl_2$ (1 × salt) 43.3 mmol/L + Dextran 5% | 4 | 1 min | 95.9 | 95.5 |

*Explanation of the appearance characteristics: 1—excellent; 2—cracked; 3—slightly reduced in volume; 4—decrease in volume/fusion; 5—complete collapse/deformation.

Medicinal forms A, C, D and E were selected for short-term accelerated stability studies at 40 and 60° C. To assess the degree of hydrolysis, the formation of Ara-CMP (in %) was evaluated. All dosage forms containing $MgCl_2$ showed similar increases in Ara-CMP content of approximately 0.4-0.5% at 40° C. 21 days after. For the samples with a molar ratio of 2:1, the formation of Ara-CMP was somewhat less than that of the samples with a molar ratio of 1:1. Eight days later, at 60° C., the Ara-CMP content increased by approximately 0.8%. The SBEβCD sample showed a larger increase in the Ara-CMP content 8 days later (0.6% at 40° C. and 1.6% at 60° C.). Approximate shelf life estimates obtained by the Arrhenius equation show that prolonged storage at 2-8° C. should ensure a shelf life of at least two years, given that the Ara-CMP level indicated in the specification should be less than 5.0%.

Investigation of the Effect of Using the Annealing Stage

To evaluate the use of the annealing stage, a dosage form with a molar ratio of $MgCl_2$ to MBC-11 (2:1) was selected as a part of the cycle. Annealing is the stage of the process, during which the samples are kept at a specific temperature below the freezing point for a certain period of time. It is used to facilitate the crystallization of active ingredients and fillers, as well as to change the shape and size of ice crystals due to Oswald ripening. Annealing can affect both the cycle time and the stability of the finished product.

The modulated DSC used to characterize the dosage form with the active substance at a concentration of 50 mg/mL showed a clear crystallization at −37° C., which had not previously been isolated from the enthalpic component (−27° C.) during rapid SWFItch to the specified temperature conditions. The observation also confirmed for what reason the fusion occurred in the sintered material during the first lyophilization cycle at the ultimate drying temperature of −26° C. The annealing phase at −35° C., which is two degrees higher than the glass transition temperature, was added into the lyophilization cycle. For lyophilization, 5 mL vials were used, each of which was filled with 2 mL of solution. As a result of the lyophilization cycle, a sintered material with no cracks was formed.

The lyophilized material was kept at 40° C. to determine stability. Hydrolysis was evaluated by the formation of Ara-CMP. 21 days (3 weeks) after, the Ara-CMP content increased by 0.4%, which was similar to the sample obtained using the lyophilization cycle without the annealing stage.

Despite the fact that the annealing step does not have clear advantages or disadvantages in relation to chemical stability, it is recommended to use it for obtaining larger and more homogeneous crystals, thereby increasing the efficiency of the cycle.

Stability of the Proposed Solutions to be Filled into Vials for Lyophilization

Several studies of the stability of the proposed solutions to be filled into the vials for lyophilization were performed. During the first study, the following solutions were evaluated at 2-8° C., 25° C. and ambient temperature for 30 hours (Table 6). The amount of MBC-11 was 100 mg per bottle.

TABLE 6

Proposed solutions to be filled into

| Formulation composition | MBC-11 (mg/mL) | Volume of solution to be filled into (ml) |
|---|---|---|
| $MgCl_2$:MBC-11 (2:1) | 50 | 2 |
| $MgCl_2$:MBC-11 (1:1) and Dextran-40 5% | 50 | 2 |
| $MgCl_2$:MBC-11 (2:1) and Dextran-40 5% | 25 | 4 |
| $MgCl_2$:MBC-11 (2:1) and Dextran-40 10% | 25 | 4 |

All solutions with a $MgCl_2$: MBC-11 molar ratio of 2:1 showed in general identical levels of MBC-11 degradation (an increase in Ara-CMP content of 0.75% within 30 hours at ambient temperature). At the same time, the content of Ara-CMP in a solution with a ratio of 1:1 in most cases was approximately 0.1-0.3% higher. This result is consistent with other observations, attesting to the fact that when the ratio of stabilizer to conjugate is increased from 1:1 and more, the hydrolytic stability of the solutions increases. The amount of MBC-11 or the amount of dextran present does not have a significant effect on chemical stability.

Investigation of Physical Stability of Solutions to be Filled into

As mentioned earlier, the use of divalent cations leads to physical instability, namely, an insoluble precipitate can be formed as a result of the use of divalent cations. Studies were therefore conducted to evaluate the physical stability of solutions containing different concentrations of etidronate-cytarabine conjugate (10 mg/mL to 50 mg/mL) with $MgCl_2$ to drug ratio of 1:1 to 10:1. The solutions prepared were stored in glass bottles, some of them were filtered through a 0.2 μm polyvinylidene fluoride (PVDF) membrane. The study was performed at 2-8° C. and room temperature.

A decrease in the total concentration of MBC-11 in a solution for filling vials for lyophilization in general improved the physical stability of solutions obtained by dissolving the lyophilizate. All solutions with a concentration of 10 mg/mL under both conditions (i.e., at 2-8° C. and room temperature) were physically stable for 27 hours. 27 hours later, some precipitation showed in one of the samples stored at 2-8° C. Solutions with a concentration of 25 mg/mL were stable for 24 hours. After 24 hours, several dosage forms showed signs of precipitation. In solutions with a concentration of 25 mg/mL, a precipitate was observed at 2-8° C. 8 hours after. Also, the chemical stability was monitored during the study, and the data obtained corresponded to the results of previous studies. The summary tables of physical observations are presented below.
Code of visual observation results:
\* transparent solution (no solid particles),
\*\* small flakes,
\*\*\* large white flakes.

TABLE 7

Results of visual observations of solutions for filling at 2-8° C.

| Dosage form code | Formulation composition | Time (hours) | | | | | | | |
|---|---|---|---|---|---|---|---|---|---|
| | | t = 0 | t = 2 | t = 4 | t = 8 | t = 24 | t = 27 | t = 30 | t = 48 |
| F1a-NF | 50 mg/mL MBC-11 trisodium salt and 173 mmol/L $MgCl_2$ (no filtration after preparation) | * | * | * | ** | *** | *** | *** | *** |
| F1a-F | 50 mg/mL MBC-11 trisodium salt and 173 mmol/L $MgCl_2$ (filtered after preparation) | * | * | * | * | *** | *** | *** | *** |
| F2a-NF | 50 mg/mL MBC-11 trisodium salt and 86.5 mmol/L $MgCl_2$ (no filtration after preparation) | * | * | * | * | *** | *** | *** | *** |
| F2a-F | 50 mg/mL MBC-11 trisodium salt and 86.5 mmol/L $MgCl_2$ (filtered after preparation) | * | * | * | * | * | *** | *** | *** |
| F1b-NF | 25 mg/mL MBC-11 trisodium salt and 173 mmol/L $MgCl_2$ (no filtration after preparation) | * | * | * | * | * | * | * | ** |
| F1b-F | 25 mg/mL MBC-11 trisodium salt and 173 mmol/L $MgCl_2$ (filtered after preparation) | * | * | * | * | * | * | * | ** |
| F2b-NF | 25 mg/mL MBC-11 trisodium salt and 86.5 mmol/L $MgCl_2$ (no filtration after preparation) | * | * | * | * | * | ** | ** | ** |

TABLE 7-continued

Results of visual observations of solutions for filling at 2-8° C.

| Dosage form code | Formulation composition | t = 0 | t = 2 | t = 4 | t = 8 | t = 24 | t = 27 | t = 30 | t = 48 |
|---|---|---|---|---|---|---|---|---|---|
| F2b-F | 25 mg/mL MBC-11 trisodium salt and 86.5 mmol/L MgCl$_2$ (filtered after preparation) | * | * | * | * | * | * | * | ** |
| F1c-NF | 10 mg/mL MBC-11 trisodium salt and 173 mmol/L MgCl$_2$ (no filtration after preparation) | * | * | * | * | * | * | * | * |
| F1c-F | 10 mg/mL MBC-11 trisodium salt and 173 mmol/L MgCl$_2$ (filtered after preparation) | * | * | * | * | * | * | * | * |
| F2c-NF | 10 mg/mL MBC-11 trisodium salt and 86.5 mmol/L MgCl$_2$ (no filtration after preparation) | * | * | * | * | * | * | * | ** |
| F2c-F | 10 mg/mL MBC-11 trisodium salt and 86.5 mmol/L MgCl$_2$ (filtered after preparation) | * | * | * | * | * | * | * | * |

TABLE 8

Results of visual observations of solutions for filling at room temperature.

| Dosage form code | Formulation composition | t = 0 | t = 2 | t = 4 | t = 8 | t = 24 | t = 27 | t = 30 | T = 48 |
|---|---|---|---|---|---|---|---|---|---|
| F1a-NF | 50 mg/mL MBC-11 trisodium salt and 173 mmol/L MgCl$_2$ (no filtration after preparation) | * | * | * | * | *** | *** | *** | *** |
| F1a-F | 50 mg/mL MBC-11 trisodium salt and 173 mmol/L MgCl$_2$ (filtered after preparation) | * | * | * | * | *** | *** | *** | *** |
| F2a-NF | 50 mg/mL MBC-11 trisodium salt and 86.5 mmol/L MgCl$_2$ (no filtration after preparation) | * | * | * | * | *** | *** | *** | *** |
| F2a-F | 50 mg/mL MBC-11 trisodium salt and 86.5 mmol/L MgCl$_2$ (filtered after preparation) | * | * | * | * | *** | *** | *** | *** |
| F1b-NF | 25 mg/mL MBC-11 trisodium salt and 173 mmol/L MgCl$_2$ (no filtration after preparation) | * | * | * | * | * | ** | ** | ** |
| F1b-F | 25 mg/mL MBC-11 trisodium salt and 173 mmol/L MgCl$_2$ (filtered after preparation) | * | * | * | * | * | ** | ** | ** |
| F2b-NF | 25 mg/mL MBC-11 trisodium salt and 86.5 mmol/L MgCl$_2$ (no filtration after preparation) | * | * | * | * | * | ** | ** | ** |
| F2b-F | 25 mg/mL MBC-11 trisodium salt and 86.5 mmol/L MgCl$_2$ (filtered after preparation) | * | * | * | * | * | * | * | ** |
| F1c-NF | 10 mg/mL MBC-11 trisodium salt and 173 mmol/L MgCl$_2$ (no filtration after preparation) | * | * | * | * | * | * | * | * |
| F1c-F | 10 mg/mL MBC-11 trisodium salt and 173 mmol/L MgCl$_2$ (filtered after preparation) | * | * | * | * | * | * | * | * |

TABLE 8-continued

Results of visual observations of solutions for filling at room temperature.

| Dosage form | | Time (hours) | | | | | | | |
|---|---|---|---|---|---|---|---|---|---|
| code | Formulation composition | t = 0 | t = 2 | t = 4 | t = 8 | t = 24 | t = 27 | t = 30 | T = 48 |
| F2c-NF | 10 mg/mL MBC-11 trisodium salt and 86.5 mmol/L MgCl$_2$ (no filtration after preparation) | * | * | * | * | * | * | * | * |
| F2c-F | 10 mg/mL MBC-11 trisodium salt and 86.5 mmol/L MgCl$_2$ (filtered after preparation) | * | * | * | * | * | * | * | * |

Thus, as a result of the studies performed, it was found that when the ratio of stabilizer to conjugate increases from 1:1, the physical stability of the solutions increases. In addition, it was found that an increase in the concentration of the etidronate-cytarabine conjugate in a solution in more than 25 mg/mL affects its physical stability adversely.

Investigation of Compatibility with the Medium for Intravenous Administration

A solution with a concentration of 25 mg/mL MBC-11 and a molar ratio of MgCl$_2$ to MBC-11 of 2:1 with dextran 5% was prepared and then diluted to a concentration of 1 mg/mL in different media for intravenous administration: phosphate buffered saline, natural saline solution, Dulbecco's phosphate buffered saline, isotonic sodium chloride solution, Lactated Ringer's Solution, and dextrose 5% in water (D5W) solution. Dextrose solution D5W showed the lowest degradation of MBC-11; the Ara-CMP content increased by 1% within one day. This increase was similar to an aqueous control sample, indicating that dextrose does not adversely affect the active pharmaceutical ingredient MBC-11.

Investigation of Physical and Hydrolytic Stability of Reconstituted Lyophilizates A reconstituted lyophilisate of the following composition was used in the following study, calculated as one vial:

| Filling volume | Amount of MBC-11 (mg) | Amount of MBC-11 (µmol) | Amount of MgCl$_2$ (mg) | Amount of MgCl$_2$ (µmol) |
|---|---|---|---|---|
| 5 mL | 100 | 173 | 32.9 | 346 |

The lyophilized dosage form was evaluated for compatibility with three different media for intravenous administration within 24 hours: sterile water for injection (SWFI), D5W and 0.9% sodium chloride solution. Low and high infusion doses for clinical use were investigated, they amounted to 0.25 mg/mL and 10 mg/mL MBC-11 in the solution, respectively. The lyophilized dosage form was first dissolved in 5 mL SWFI to the MBC-11 concentration of 20 mg/mL, and then it was placed in glass vials and diluted with each medium for intravenous administration until the infusion doses under study were obtained. The solutions thus obtained were kept at 2-8° C. and 25° C. for 24 hours, and the evaluation of the samples in appearance, content and purity at the points t=0, 2, 4, 6 and 24 hours was performed.

At each control point, solutions for intravenous administration with a high dosage were evaluated in appearance, after which they were diluted to a nominal analytical concentration of 1 mg/mL with a solvent used in the analytical method for evaluating the substance purity. The samples thus obtained were used to determine the purity and content of the active pharmaceutical ingredient.

The results showed that samples with a low concentration were physically stable within 24 hours. Samples containing a high dose were physically stable up to 6 hours. Based on the data obtained in 6 hours, the best chemical stability was achieved when D5W or water was used. For all dosage form solutions prepared, the maximum increase in Ara-CMP was 1.4% in low-dose sodium chloride-based intravenous media stored at 25° C. for 6 hours. For comparison, a sample with a low dose of MBC-11 in D5W showed only a 0.5% increase in the Ara-CMP content under the same conditions.

An Example of the Preparation of a Medicinal Drug According to the Invention

We weigh 14.1±0.1 g magnesium chloride hexahydrate in the clean 1 L bottle. Add 985.9±1.0 g sterile water for injection to the same bottle. Mix the resulting mixture with a magnetic stirrer at room temperature until completely dissolved.

Weigh 15.69±0.05 g MBC-11 trisodium salt (corrected for water content only) in 1 L bottle. Further, add 744.1±3.0 g the magnesium chloride solution, prepared above, to the same bottle. Mix the resulting mixture at room temperature until completely dissolved. Take a 3 mL aliquot to monitor the pH. Filter the resulting solution aseptically through a 0.2 µm polyvinylidene fluoride (PVDF) membrane into a sterile container using a Millipore SCGVU11RE filter apparatus. Pour the resulting filtrate into 20 mL glass bottles, 5.4 mL of the filtrate into each glass bottle, and lyophilize them.

Vials with the finished product, partially sealed with a rubber stopper, are completely sealed by hold-down plates of the freezer chamber and pressurized with aluminum and plastic caps, and then placed into a cooler for storage at 2-80° C.

For intravenous administration, a reconstituted lyophilizate solution is prepared by preferably dissolving the contents of the vial in water or 5DW so that the drug concentration is not more than 10 mg/mL. It was found that the reconstituted drug solution does not have physical stability at high concentrations. The reconstituted solution thus obtained is transferred to an standard volume infusion bag containing natural saline solution or 5DW. The number of vials with reconstituted lyophilizate solution per infusion bag is determined according to the dosage prescribed by the doctor.

An Example of Preparation of Solutions for Infusion Administration

To prepare solutions for intravenous infusion (drop) administration, a medicinal drug is used in the form of a lyophilisate (pharmaceutical composition) of the following composition (per one 20 ml vial):

| Substance name | Amount, mg |
| --- | --- |
| Active substance (active component): | |
| trisodium salt of 1-((((((2R,3S,4S,5R)-5-(4-amino-2-oxopyrimidine-1(2H)-yl)-3,4-dihydroxytetrahydrofuran-2-yl)methoxy))(hydroxy)phosphoryloxy)(hydroxy)phosphoryl)-1-hydroxyethylphosphonic acid | 110.5 mg |
| (on dry anhydrous basis, free acid) | (100.00 mg) |
| Adjuvant: | |
| Magnesium chloride | 33.00 mg |

To obtain a reconstituted solution, 10 ml of water for injections are added to the vial comprising the medicinal drug (to obtain a solution with a concentration of 10 mg/ml on free acid basis), the contents of the vial are mixed with light shaking movements, preventing foaming. The time of lyophilisate dissolution is not more than 5 minutes. The reconstituted solution is stored in a vial for not more than one hour at a temperature of 2-8° C. Before administering to a patient, the prepared reconstituted solution of the medicinal drug is diluted in 5% dextrose (glucose) solution for injections (D5W) up to a cumulative volume of 500 ml by sterile transfer of the reconstituted solution of the medicinal drug to an infusion pack comprising the calculated amount of D5W.

The number of vials with the reconstituted lyophilisate solution per one infusion pack is determined so as to provide the required daily dose of the active component (trisodium salt of the etidronate conjugate with cytarabine on free acid basis) to administer into a patient. To ensure the therapeutic effect, the concentration of etidronate conjugate and cytarabine on free acid basis should be 0.01-5 mg/ml-in the solution. In most preferred embodiments, the concentration of etidronate conjugate with cytarabine on free acid basis is 0.04-2 mg/ml in the solution.

The amount of the lyophilisate (i.e. the medicinal drug, which is a lyophilisate for solution for parenteral administration, including the following components: pharmaceutically acceptable salt of the divalent metal and 1-((((((2R, 3S,4S,5R)-5-(4-amino-2-oxopyrimidine-1(2H)-yl)-3,4-dihydroxytetrahydrofuran-2-yl)methoxy))(hydroxy)phosphoryloxy)(hydroxy)phosphoryl)-1-hydroxyethylphosphonic acid or pharmaceutically acceptable salt hereof, in a molar ratio of components ranging from 1:1 to 20:1, which should be taken to obtain a solution of the required concentration, can be calculated based on known calculations and based on data on a therapeutically effective amount of the medicinal drug given in the application documents according to the invention.

As mentioned above, the daily dose for each patient is calculated individually, based on a therapeutically effective amount, dependent on the patient's general state, the severity of the disease, the method, the drug administration regimen, the combined treatment with other drugs and other antitumor therapy, etc., and may be 0.001-50 mg/kg, more preferably, 0.001-25 mg/kg, even more preferably 0.1-10 mg/kg, 0.1-6 mg/kg, most preferably 0.5-5 mg/kg (on active compound basis, i.e. free acid of conjugate etidronate with cytarabine, per patient's weight).

The duration of intravenous infusion is about 2 hours, more preferably, not more than 2 hours.

The given method of solution preparation can be modified in accordance with the accepted methods of preparing solutions for intravenous drop infusion. For example, the volume of the injected solution can vary from 100 to 1,000 ml, while the daily dose can be administered one or several times, depending on the individual characteristics of a patient. Dilution of lyophilisate in two stages, as indicated above in the given example, is also not necessary and the only method to obtain the solution with the required concentration.

Drug Efficacy and Safety Study According to the Invention in the Treatment of Bone Lesions, Caused by Malignant Neoplasms To assess the efficacy and safety of the novel medicinal drug, clinical studies of phase I were conducted according to "Open non-randomized multicenter clinical study" protocol. The doses of the medicinal drug were studied calculated as 0.5 mg/kg, 1.0 mg/kg, 2.5 mg/kg, 5 mg/kg, 10 mg/kg of the active component (etidronate conjugate with cytarabine on free acid basis) within the protocol framework.

Patients were administered with a solution for parenteral administration, obtained by dissolving the pharmaceutical composition according to the invention, which is a lyophilisate for solution for parenteral administration, including magnesium chloride and trisodium salt of etidronate conjugate with cytarabine, in a molar ratio of 2:1, in a pharmaceutically acceptable solvent prepared by the method disclosed above.

As a result of the experiments, it was found that the maximum tolerated daily dose of the active substance is 5 mg/kg. Doses exceeding 5 mg/kg are also effective, but less recommended due to worse tolerability. A good safety and efficacy profile has been identified for doses of 0.5 mg/kg, 1.0 mg/kg, 2.5 mg/kg, 5 mg/kg.

A total of 16 patients with bone lesions caused by malignant neoplasms took part in the study, 15 patients of them received single and multiple dosing with the study drug, 1 patient discontinued participation in the study after a single dosing due to an adverse event not related to the study drug. A total of 5 patient cohorts have been studied (3 people in each), with dose levels of 0.5 mg/kg, 1.0 mg/kg, 2.5 mg/kg, 5 mg/kg, 10 mg/kg. All patients received a single dosing with the study drug in a dose corresponding to the dose level of the cohort with the subsequent weekly follow-up period and at least 2 cycles of multiple dosing. The cycle consisted of daily administration (o.d.) of the drug for 5 days, followed by a break of 23 days. In cohort 5 with a dose level of 10 mg/kg, the dose-limiting toxicity (DLT) was reported in two of 3 patients (grade 4 thrombocytopenia and grade 4 neutropenia). According to protocol criteria, the maximum tolerated dose is considered a dose 1 level lower than DLT (5 mg/kg). Of 206 reported foci with bone lesions caused by malignant neoplasms, in 53.8% of cases there was a decrease in the level of standardized accumulation of the radiopharmaceutical agent (2-fluoro-2-deoxy-D-glucose (FDG), determined according to the standard PET-CT procedure) in metastatic bone foci by 25% or more.

As a result of the studies it was found that the most optimal is the administration of the drug solution in a volume of 500 ml during 2 hours, although other administration regimens may be effective.

To achieve a therapeutic effect, the following treatment regimens can be used, but not limited to:

daily infusions of the drug solution for 5 days followed by a break of at least 23 days;

daily infusions of the drug solution for 5 days followed by a break for 23-40 days;

infusions of the drug solution in the mode of 3 administrations every other day followed by a break of at least 23 days;

infusions of the drug solution in the mode of at least one administration per week for 12 months;

infusions of the drug solution in the mode of at least one administration per month for 12 months;

The number of cycles disclosed above is usually 1-12 per a treatment course.

In certain embodiments, the number of cycles is 1-6 per a treatment course.

The treatment regimen, as well as the duration of treatment, can also vary from patient to patient and range from the minimum course of treatment to conducting treatment by courses throughout the patient's life. In addition, a combination of different treatment regimens for one patient during the course of his treatment is also possible.

The clinical examples of treating patients with the drug according to the invention are given below.

EXAMPLE 1

Patient E. (sex—female), diagnosis—advanced breast cancer. Multiple metastases in the cranial roof bones, cervical, thoracic and lumbar spine, clavicle, sternum, humeri, iliac bones.

She received treatment with the drug according to the invention (solution of magnesium chloride lyophilisate and trisodium salt of etidronate conjugate with cytarabine with a molar ratio of the components of 2:1, in a pharmaceutically acceptable solvent) at a dose of 0.5 mg/kg. A partial metabolic response of bone metastatic foci was reported after 2 cycles of drug application according to PET-CT (positron-emission tomography and computed tomography) results. She received 4 cycles of therapy with the study drug: daily administration during 5 days followed by a break of 23 days.

As a result of the treatment, the metabolic activity of bone foci in the sternum, left clavicle and right humerus is not noted (100% decrease in activity). A decrease in the level of metabolic activity was also noted in the iliac bone (by 55%), the lumbar vertebrae (by 57%), the cervical vertebrae (by 72%), the thoracic vertebrae.

EXAMPLE 2

Patient K. (sex—female), diagnosis—advanced breast cancer. Multiple foci of destruction and sclerosis in the cranial roof bones, mandible, cervical, thoracic, lumbar vertebrae, sacrum, pubic and iliac bones, ribs, collarbones, shoulder blades, pelvic bones, femora, humeri, with pathological fractures of ribs, bodies of all thoracic and lumbar vertebrae.

She received treatment with the drug according to the invention (solution of magnesium chloride lyophilisate and trisodium salt of etidronate conjugate with cytarabine with a molar ratio of the components of 2:1, in a pharmaceutically acceptable solvent) at a dose of 2.5 mg/kg. She received 4 cycles of therapy with the study drug: daily administration during 5 days followed by a break of 23 days.

As a result of the treatment, there was a regression of metabolic activity in various bone metastatic foci, a stable impairment of metabolism of bone metastasis foci was reported. In particular, a decrease in the standardized level of radiopharmaceutical agent accumulation was noted in the sacrum by 20%, in the right 7th rib—by 25%, in the left pubic bone—by 30%, in the right iliac bone—by 20%.

EXAMPLE 3

Patient S. (sex—male), diagnosis—advanced prostate cancer. Multiple bone metastases (thoracic and lumbar vertebrae, iliac bones, ribs, pubic bones).

He received treatment with the drug according to the invention (solution of magnesium chloride lyophilisate and trisodium salt of etidronate conjugate with cytarabine with a molar ratio of the components of 2:1, in a pharmaceutically acceptable solvent) at a dose of 1.0 mg/kg. He received 4 cycles of therapy with the study drug: daily administration during 5 days followed by a break of 23 days.

As a result of the conducted treatment, a regression of metabolic activity in all metastatic foci was reported. Hypermetabolism was no longer noted in the bone foci in the thoracic and lumbar vertebrae (Th7, Th12, L1), the right iliac bone, the 4th, 5th and 6th ribs, the pubic bones (decrease by 100%). The level of radiopharmaceutical agent accumulation decreased by 40% in the left iliac bone.

EXAMPLE 4

Patient P. (sex—female), diagnosis—advanced breast cancer. Multiple bone metastases (sacrum, iliac bones, sternum, acetabulum).

She received treatment with the drug according to the invention (solution of magnesium chloride lyophilisate and trisodium salt of etidronate conjugate with cytarabine with a molar ratio of the components of 2:1, in a pharmaceutically acceptable solvent) at a dose of 5.0 mg/kg. She received 2 cycles of therapy with the study drug: daily administration during 5 days followed by a break of 23 days.

As a result of the treatment, a stable metabolic disturbance was registered in all metastatic foci. There is a decrease in the level of metabolism in the target foci (sacrum and iliac bone) by 10% and 50%, respectively, a decrease of 5-15% is noted for non-target foci.

Despite the fact that the invention has been described with reference to the disclosed embodiments, it should be apparent to those skilled in the art that the specific, detailed experiments described are for the purpose of illustrating the present invention only, and should not be construed as in any way limiting the scope of the invention. It should be understood that various modifications are possible without deviation from the chief matter of the present invention.

The invention claimed is:

1. A method for treating bone lesions caused by malignant neoplasms, the method comprising parenterally administering to a patient with bone lesions a solution of a lyophilisate in a pharmaceutically acceptable solvent, said lyophilisate including the following components:

a first component comprising magnesium chloride or calcium chloride and a second component comprising 1-((((((2R,3S,4S,5R)-5-(4-amino-2-oxopyrimidine-1(2H)-yl)-3,4-dihydroxytetrahydrofuran-2-yl)methoxy))(hydroxy)phosphoryloxy)(hydroxy)phosphoryl)-1-hydroxyethylphosphonic acid or pharmaceutically acceptable salt hereof, with a molar ratio of the first component to the second component ranging from 1:1 to 20:1, the concentration of the 1-((((((2R,3S,4S,5R)-5-(4-amino-2-oxopyrimidine-1(2H)-yl)-3,4-dihydroxytetrahydrofuran-2-yl)methoxy))(hydroxy)phosphoryloxy)(hydroxy)phosphoryl)-1-hydroxyethylphosphonic acid or its pharmaceutically acceptable salt in terms of the free acid, in solution is 0.01-5 mg/ml.

2. The method according to claim 1, wherein the pharmaceutically acceptable salt of 1-((((((2R,3S,4S,5R)-5-(4-amino-2-oxopyrimidine-1(2H)-yl)-3,4-dihydroxytetrahydrofuran-2-yl)methoxy))(hydroxy)phosphoryloxy)(hydroxy)phosphoryl)-1-hydroxyethylphosphonic acid is a trisodium salt.

3. The method according to claim 1, wherein the molar ratio of the pharmaceutically acceptable salt of the divalent metal to 1-((((((2R,3S,4S,5R)-5-(4-amino-2-oxopyrimidine-1(2H)-yl)-3,4-dihydroxytetrahydrofuran-2-yl)methoxy))(hydroxy)phosphoryloxy)(hydroxy)phosphoryl)-1-hydroxyethylphosphonic acid or pharmaceutically acceptable salt hereof is ranging from 1:1 to 12:1.

4. The method according to claim 1, wherein the molar ratio of the pharmaceutically acceptable salt of the divalent metal to 1-((((((2R,3S,4S,5R)-5-(4-amino-2-oxopyrimidine-1(2H)-yl)-3,4-dihydroxytetrahydrofuran-2-yl)methoxy))(hydroxy)phosphoryloxy)(hydroxy)phosphoryl)-1-hydroxyethylphosphonic acid or pharmaceutically acceptable salt hereof is ranging from 1:1 to 2:1.

5. The method according to claim 1, wherein the molar ratio of the pharmaceutically acceptable salt of the divalent metal to 1-((((((2R,3S,4S,5R)-5-(4-amino-2-oxopyrimidine-1(2H)-yl)-3,4-dihydroxytetrahydrofuran-2-yl)methoxy))(hydroxy)phosphoryloxy)(hydroxy)phosphoryl)-1-hydroxyethylphosphonic acid or pharmaceutically acceptable salt hereof is 2:1.

6. The method according to claim 1, wherein the pharmaceutically acceptable solvent is a 5% aqueous dextrose solution and/or sterile water for injections.

7. The method according to claim 1, wherein the parenteral administration is an administration in the form of an intravenous drop infusion.

8. The method according to claim 1, wherein the concentration of the 1-((((((2R,3S,4S,5R)-5-(4-amino-2-oxopyrimidine-1(2H)-yl)-3,4-dihydroxytetrahydrofuran-2-yl)methoxy))(hydroxy)phosphoryloxy)(hydroxy)phosphoryl)-1-hydroxyethylphosphonic acid or its pharmaceutically acceptable salt in terms of the free acid, in solution is 0.04-2 mg/ml.

9. The method according to claim 1, wherein the 1-((((((2R,3S,4S,5R)-5-(4-amino-2-oxopyrimidine-1(2H)-yl)-3,4-dihydroxytetrahydrofuran-2-yl)methoxy))(hydroxy)phosphoryloxy)(hydroxy)phosphoryl)-1-hydroxyethylphosphonic acid or its pharmaceutically acceptable salt in terms of the free acid, is administered in a dose of 0.5 to 5 mg/kg in the form of an intravenous drop infusion.

10. The method according to claim 9, wherein the solution in a volume of 500 ml is administered to a patient.

11. The method according to claim 9, wherein the infusions are performed in cycles: daily administration during 5 days followed by a break of at least 23 days.

12. The method according to claim 11, wherein the infusions are performed in cycles: daily administration during 5 days followed by a break during 23-40 days.

13. The method according to claim 9, wherein the infusions are performed in cycles: 3 administrations every other day followed by a break of at least 23 days.

14. The method according to claim 9, wherein the infusions are performed in cycles: at least one administration per week for 12 months.

15. The method according to claim 9, wherein the infusions are performed in cycles: at least one administration per month for 12 months.

16. The method according to claim 11, wherein the number of cycles is 1-12 per a treatment course.

17. The method according to claim 11, wherein the number of cycles is 1-6 per a treatment course.

18. The method according to claim 1, wherein the bone lesion caused by malignant neoplasms is primary bone cancer, multiple myeloma, metastatic bone tissue lesions caused by breast cancer, prostate cancer or thyroid cancer, lung cancer, kidney cancer, gastrointestinal cancer, ovarian cancer, melanoma, lymphoma, or malignant neoplasms in other tissues and organs.

19. The method according to claim 18, wherein the primary bone cancer is osteosarcoma, Ewing sarcoma, chondrosarcoma, fibrosarcoma, malignant fibrous histiocytoma, giant-cell tumour of the bone or chordoma.

\* \* \* \* \*